US008649018B2

(12) United States Patent
Dell et al.

(10) Patent No.: US 8,649,018 B2
(45) Date of Patent: Feb. 11, 2014

(54) OPTICAL CANTILEVER BASED ANALYTE DETECTION

(75) Inventors: John Marcel Dell, Bull Creek (AU); Mariusz Martyniuk, Wattle Grove (AU); Adrian John Keating, Mt. Hawthorn (AU); Gino Michael Putrino, Dianella (AU); Lorenzo Faraone, Mt. Lawley (AU)

(73) Assignee: University of Western Australia, Crawley (AU)

( * ) Notice: Subject to any disclaimer, the term of this patent is extended or adjusted under 35 U.S.C. 154(b) by 6 days.

(21) Appl. No.: 13/035,374

(22) Filed: Feb. 25, 2011

(65) Prior Publication Data

US 2012/0218559 A1     Aug. 30, 2012

(51) Int. Cl.
*G01B 9/02*     (2006.01)
(52) U.S. Cl.
USPC .......................................... 356/480
(58) Field of Classification Search
USPC .......................................... 356/480
See application file for complete search history.

(56) References Cited

U.S. PATENT DOCUMENTS

| 6,987,898 | B2 * | 1/2006 | Tran et al. | 385/13 |
| 7,671,511 | B2 * | 3/2010 | Battiston | 310/316.01 |
| 2007/0093971 | A1 * | 4/2007 | Candy et al. | 702/27 |

OTHER PUBLICATIONS

G. Putrino et al. (2010. E-ISBN 978-1-4244-7333-5, IEEE, Comparison of Dynamic and static operation of a novel optical read-out technology for micromachined cantilever sensors, hereinafter Putrino).*
Kauppinen, L.J., et al., "Grated Waveguide Optical Cavity as a Compact Sensor for Sub-nanometre Cantilever Deflections", ECIO, MESA Research Institute for Nanotechnology, University of Twente, 7500 AE Enschede, Jun. 11-13, 2008, pp. 111-114, Eindhoven, The Netherlands.
Pham, S.V., et al., "Read-Out of Cantilever Bending With a Grated Waveguide Optical Cavity", IEEE Photonics Technology Letters, Feb. 15, 2011, pp. 215-117, vol. 23, No. 4.
Lavrik et al., "Cantilever transducers as a platform for chemical and biological sensors", Rev. Sci. Instrum., Jul. 2004, pp. 2229-2253, vol. 74, No. 7, AIP Publishing LLC.
Comittee on Assessment of Security Technologies for Transportation, National Research Council, "Opportunities to Improve Airport Passenger Screening with Mass Spectrometry", The National Academies Press, 2004, 56 pages, Washington DC.
Canas et al., "Mass spectrometry technologies for proteomics", Briefings in Functional Genomics and Proteomics, Feb. 3, 2006, pp. 295-320, vol. 4, No. 4, Oxford University Press.
Wapelhorst et al., "Complex MEMS: a fully integrated TOF micro mass spectrometer", Sensors and Actuators A, 2007, pp. 22-27, vol. 138, Elsevier B.V.

(Continued)

*Primary Examiner* — Tarifur Chowdhury
*Assistant Examiner* — Sunghee Y Gray
(74) *Attorney, Agent, or Firm* — Howard & Howard Attorneys PLLC

(57) ABSTRACT

An apparatus for detecting a presence of one or more analytes in a sample. The apparatus comprises a cantilever (205) and a grating coupled resonating structure (210). The cantilever (205) comprises an analyte selective coating that is selective to the one or more analytes. The grating coupled resonating structure (210) is positioned adjacent to the cantilever (205). The first grating coupled resonating structure comprises a first interrogating grating coupler (220) which together with the cantilever forms an optical resonant cavity.

20 Claims, 9 Drawing Sheets

(56) References Cited

OTHER PUBLICATIONS

Loui et al., "Chemical vapor discrimination using a compact and low-power array of piezoresistive microcantilevers", The Analyst (The Royal Society of Chemistry), May 2008, pp. 608-615, vol. 133, No. 5, RSC Publishing.

Baller et al., "A cantilever array-based artificial nose", Ultramicroscopy, 2000, pp. 1-9, vol. 82, Elsevier Science B.V.

Brereton, "Chemometrics: Data Analysis for the Laboratory and Chemical Plant", 2003, University of Bristol, UK, pp. 1-489, John Wiley & Sons Ltd, The Atrium, Southern Gate, Chichester, West Sussex, PO 19 8SQ, England.

Yang et al., "Zeptogram-Scale Nanomechanical Mass Sensing", Nano Letters, Apr. 2006, pp. 583-586, vol. 6, No. 4, The American Chemical Society.

Li et al., "Ultra-sensitive NEMS-based cantilevers for sensing, scanned probe and very high-frequency applications", Nature Nanotechnology, 2007, 3 pages, vol. 2, Issue 2.

Stievater et al., "All-optical micromechanical chemical sensors", Appl. Phys. Lett., 2006, pp. 091125-1-091125-3, vol. 89, AIP Publishing LLC.

Kong et al., "A MEMS Sensor Array for Explosive Particle Detection", Proc. IEEE Int. Conf. Inform., 2004, pp. 278-281.

Xu et al., "Optical Polymer Waveguide Based Cantilevers for Chemical and Biological Sensors", IEEE Sensors Conf., 2005, pp. 963-966, IEEE.

Taillaert et al.,"Grating Couplers for Coupling between Optical Fibers and Nanophotonic Waveguides", Japanese Journal of Applied Physics, 2006, pp. 6071-6077, vol. 45, No. 8A.

Jalali et al., "Silicon Photonics", Journal of Lightwave Technology, Dec. 2006, pp. 4600-4615, vol. 24, No. 12, IEEE.

See http://www.epixfab.eu/—webpage attached.

Martyniuk et al., "Stress in low-temperature plasma enhanced chemical vapour deposited silicon nitride thin films", Smart Materials and Structures, 2006, pp. S29-S38, vol. 15, Institute of Physics Publishing, UK.

Huang et al., "Design and Development of Tunable Filters for MEMS Adaptive Infrared Detectors", Nanotechnology and Precision Engineering, Mar. 2006, pp. 38-45, vol. 4, No. 1.

Huang et al., "Effect of deposition conditions on mechanical properties of low-temperature PECVD silicon nitride films", Materials Science and Engineering A 435-436, 2006, pp. 453-459, Elsevier B.V.

Martyniuk et al., "Dielectric thin films for MEMS-based optical sensors", Microelectronics Reliability, 2007, pp. 733-738, vol. 47, Elsevier Ltd.

Walmsley et al., "Process condition dependence of mechanical and physical properties of silicon nitride thin films", J. Appl. Phys., 2007, pp. 103517-1-103517-6, vol. 102, AIP Publishing LLC.

Hickman et al., "Selective Functionalization of Gold Microstructures with Ferrocenyl Derivatives via Reaction with Thiols or Disulfides: Characterization by Electrochemistry and Auger Electron Spectroscopy", J. Am. Chem. Soc., 1991, pp. 1128-1132, vol. 113, American Chemical Society.

Boiadjiev et al., "Photochemical Hydrosilylation of 11-Undecenyltriethylammonium Bromide with Hydrogen-Terminated Si Surfaces for the Development of Robust Microcantilever Sensors for Cr(VI)", Langmuir—The ACS Journal of Surfaces and Colloids, Feb. 15, 2005, pp. 1139-1142, vol. 21, No. 4, American Chemical Society.

Langner et al., "Controlled Silicon Surface Functionalization by Alkene Hydrosilylation", J. Am. Chem. Soc., 2005, pp. 12798-12799, vol. 127, American Chemical Society.

Hsieh et al., "Limits of Recognition for Simple Vapor Mixtures Determined with a Microsensor Array", Anal. Chem., 2004, pp. 1885-1895, vol. 76, American Chemical Society.

MEEP from AbInitio, printed Aug. 28, 2013—available at ab-initio.mit.edu/wiki/index.php/Meep, pp. 1-3.

* cited by examiner

OPTICAL CANTILEVER BASED ANALYTE DETECTION

FIELD OF THE INVENTION

The present invention relates to an apparatus and method for detecting analytes, and more particularly to detecting analytes in a sample using optical cantilevers.

BACKGROUND OF THE INVENTION

Different methods for detecting chemical and biological analytes have been used. Such technology has been used, for example, in process control, environmental monitoring, medical diagnostics and security.

Mass spectroscopy is one approach to detect such analytes. The process begins with an ionized sample. The ionized sample is shot through a vacuum that is subjected to an electromagnetic field. The electromagnetic field changes the path of lighter ions more than heavier ions. A series of detectors or a photographic plate are then used to sort the ions depending on their mass. The output of this process, which is the signal from the detectors or the photographic plate, can be used to determine the composition of the analytes in the sample.

A disadvantage of mass spectroscopy instruments is that they are generally high-cost instruments. Additionally, they are difficult to ruggedize, and are not useful for applications that require a sensor head to be remote from signal-processing electronics.

A more recent approach is to use Micro Electro Mechanical Systems (MEMS)-based microstructures, and more specifically micro-cantilevers. These are extremely sensitive systems, and several demonstrations of mass sensors that have detection limits as low $10^{-21}$ g, approximately the mass of a single protein molecule, have been performed. While these experiments have been performed in idealised environments, practical cantilever-based systems have been demonstrated for the detection of a wide range of single analytes.

A portion of the micro-cantilever is coated with an analyte selective coating to which the analyte is adsorbed.

There are two common modes of operation of micro-cantilever sensors, namely static and dynamic.

In the static mode, a stress differential is induced across the cantilever due to preferential adsorption of an analyte onto the analyte selective coating causing the cantilever to bend. The extent of the bending is in direct relation to the amount of analyte adsorbed. The stress differential can be induced by the analyte causing swelling of an overlayer, or by changes in the Gibbs free energy of the surface.

In the dynamic mode, the adsorbed analyte changes the mass of the cantilever and hence its mechanical resonance frequency. The rate and size of the change in resonance frequency is then measured to estimate the analyte concentration. Active sensing using these structures is achieved by resonant excitation.

In general, long, compliant cantilevers are required for sensitive static sensors, while high sensitivity for dynamic sensors dictate that short, stiff beams with high Q-factor mechanical resonances are needed. The most sensitive MEMS-based sensors to date have been based on measurements of resonant frequency.

Readout technologies used with micro-cantilever sensors are primarily based on optical techniques developed for atomic force microscopy (AFM) analysis. Here, light is reflected from the cantilever tip to a distant quadrant detector, which process is referred to as optical leveraging. Electrical sensing and optical sensing techniques are also used. Electrical sensing includes piezoresistive, piezoelectric, capacitive, Lorentz force/emf sensing and tunnelling current techniques. Optical sensing techniques include optical sensing based on optical interference, the optical interference being either in an interferometer or in the use of diffraction from an optical grating formed by a line of cantilevers. This latter configuration using an optical grating formed by a line of cantilevers is often described as an array in literature, but is still effectively a sensor for a single analyte.

Another approach to analyte detection is where large, compact, integrated arrays of individual sensors are used, particularly for multi-analyte, multi-analysis applications. These are particularly useful when an unknown substance is to be identified or if there is a number of chemical species to be tested for simultaneously. Examples of such requirements can be found in the screening of food for pesticide residues where there are many different potential contaminants, detection of different antibodies in a single blood sample, or the presence of any of the many possible illicit drugs or explosives in luggage. Additionally, an array of sensors can also give significantly improved statistics of detection (including fewer false-positives and false-negatives) by averaging the response over a large number of sensors, and allows the use of multivariate statistical chemometric techniques, as are typically applied in spectroscopic analysis.

There are several disadvantages with the sensors of today. There is, for example, a lack of compact, robust and cost-effective read-out technology that combines high sensitivity with high dynamic range. Sensors that are good at detecting small amounts of analyte typically have poor dynamic range which is especially noticeable when the levels of analyte are large. A problem with AFM-based cantilever systems is that they are very large as they incorporate bulky free space optics requiring a sensor for each cantilever output. A problem with electrical cantilever systems is that they require extensive power on-chip electronics.

The present invention is aimed at one or more of the problems set forth above.

SUMMARY OF THE INVENTION

In one embodiment, the invention resides in an apparatus for detecting a presence of one or more analytes in a sample, the apparatus comprising a first cantilever comprising an analyte selective coating that is selective to said one or more analytes, a first grating coupled resonating structure positioned adjacent to the cantilever and comprising a first interrogating grating coupler, wherein the first interrogating grating coupler and the cantilever form an optical resonant cavity.

The cantilever may be dynamic. Alternatively, the cantilever may be static.

In one embodiment, the apparatus may further comprise a second grating coupled resonating structure wherein the second grating coupled resonating structure comprises a second interrogating grating coupler; and the second interrogating grating coupler and the cantilever form an optical resonant cavity.

The second grating coupled resonating structure may be positioned adjacent to the first grating coupled resonating structure on an axis substantially parallel to the cantilever.

The apparatus may further comprise a signal analyser for detection of the presence of one or more analytes in the sample.

In one aspect of the present invention, the signal analyser may compare light modulated by the first grating coupled resonating structure and the cantilever with a plurality of predefined signals.

In one embodiment, the first grating coupled resonating structure provides an initial measurement, and the second grating coupled resonating structure provides a refinement of said initial measurement.

The first grating coupled resonating structure and the second grating coupled resonating structure may be used to determine a shape of the cantilever.

Optionally, the apparatus further comprises:
a second cantilever;
a second grating coupled resonating structure comprising a second interrogating grating coupler;
wherein the second interrogating grating coupler and the second cantilever form an optical resonant cavity.

In one embodiment, the first grating coupled resonating structure and the second grating coupled resonating structure are optically coupled in series.

In an other embodiment, the first grating coupled resonating structure and the second grating coupled resonating structure are optically coupled in parallel.

In another form, the invention resides in a method of detecting the presence of one or more analytes in a sample. The method comprises the steps of applying the sample to a cantilever, wherein the cantilever comprises an analyte selective coating selective to the one or more analytes, passing an optical signal through a grating coupled resonating structure, wherein the grating coupled resonating structure is arranged to form a resonant cavity with the cantilever; and analyzing the optical signal.

In one embodiment, the cantilever is dynamic, and the step of analyzing the optical signal comprises determining the resonance frequency of the cantilever and comparing the resonance frequency to known resonant characteristics of the cantilever.

Alternatively, the cantilever is static, and the analysis step comprises determining a deflection of the cantilever.

In one embodiment, the step of analyzing the optical signal comprises the step of comparing the optical signal to a plurality of predefined signals.

The method may further comprise the steps of passing a second optical signal through a second grating coupled resonating structure, wherein the second grating coupled resonating structure is arranged to form a resonant cavity with the cantilever, and analyzing the second optical signal.

In one embodiment, the step of analysing the optical signal comprises the step of estimating an initial cantilever deflection measurement, and the step of analyzing the second optical signal comprises the step of refining the initial cantilever deflection measurement.

The method may further comprise the step of estimating a shape of said cantilever, wherein the step of analysing the optical signal comprises estimating a cantilever deflection measurement at a first position, and the step of analysing the second optical signal comprises estimating a cantilever deflection measurement at a second position.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION

Figure 1:
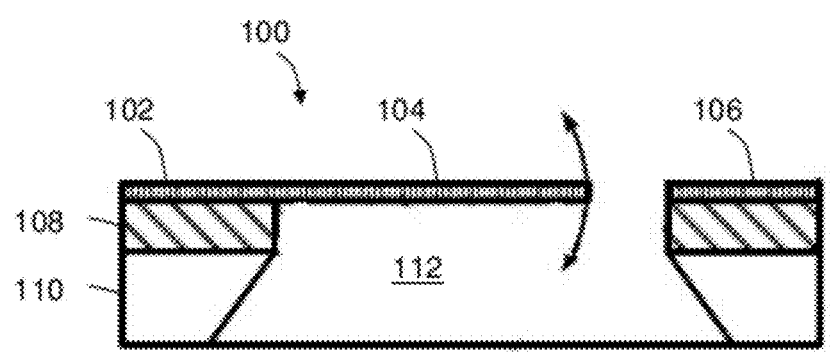
FIG. 1 shows a side sectional view of an optical microcantilever waveguide, according to the prior art.

While the present invention is open to various modifications and alternative constructions, the example embodiments shown in the drawings will be described herein in detail. It is to be understood, however, there is no intention to limit the invention to the particular example forms disclosed. On the contrary, it is intended that the invention cover all modifications, equivalences and alternative constructions falling within the spirit and scope of the invention as expressed in the appended claims.

FIG. 1 shows a side sectional view of an optical microcantilever waveguide 100, according to the prior art. The optical microcantilever waveguide 100 comprises a fixed component 102 and a dynamic component 104. The fixed component is attached to an insulator 108 such as for example $SiO_2$ or $Si3N_4$. The insulator 108 is attached to a substrate 110 such as for example a Si substrate. This layered structure allows for the simple construction of the optical microcantilever waveguide 100 through layering of the substrate 110, the insulator 108 and the optical cantilever waveguide 100, and by then etching away an area of the insulator 108 (and possibly also an area of the substrate 110) forming a void 112 under the dynamic component 104 of the optical microcantilever waveguide 100. The dynamic component 104 of the microcantilever waveguide 100 is optically coupled to a fixed waveguide 106.

The dynamic component 104 is free to move above the void 112 in the insulator 108. Upon adsorbtion of an analyte, the mass of the dynamic component 104 of the optical microcantilever waveguide 100 changes. This change in mass results in a change of a resonance frequency of the optical microcantilever waveguide 100.

Light enters at an end of the fixed component 102 of the optical microcantilever waveguide 100 and propagates along the waveguide 100 to the dynamic component 104. Light exits the dynamic component 104 in a direction towards the fixed waveguide 106.

In a dynamic mode, the light entering the fixed waveguide 106 is amplitude modulated as a result of a coupling loss between the dynamic component 104 and the fixed waveguide 106 that is in close proximity to the dynamic component 104, which loss occurs as the dynamic component 104 vibrates. The light entering the fixed waveguide 106 is nominally modulated at twice the vibration frequency of the dynamic component 104 for symmetric vibration. Alternatively, in a static mode, the dynamic component 104 of the optical microcantilever waveguide 100 may change shape upon adsorbtion of an analyte. In this case the light entering the fixed waveguide 106 has an amplitude based upon the shape of the dynamic component 104 of the optical microcantilever waveguide 100.

The light entering the fixed waveguide 106 is analysed to detect the presence of an analyte on the optical microcantilever waveguide 100. The light may be compared to light with known characteristics, such as for example light modulated due to the presence of an analyte. Alternatively, the resonance frequency or shape of the optical microcantilever waveguide 100 may be estimated and compared to pre-determined characteristics.

The present invention resides in an apparatus for detecting a presence of one or more analytes in a sample. The apparatus comprises a cantilever and a grating coupled resonating structure positioned adjacent to the cantilever. The cantilever comprises an analyte selective coating that is selective to the one or more analytes. The grating coupled resonating structure comprises an interrogating grating coupler which forms an optical resonant cavity with the cantilever.

An advantage of the present invention is the ability to economically have a very large number of sensors on a small surface, enabling efficient detection on multiple analytes. Furthermore it does not require bulky free space optics or extensive power on-chip electronics.

Figure 2:
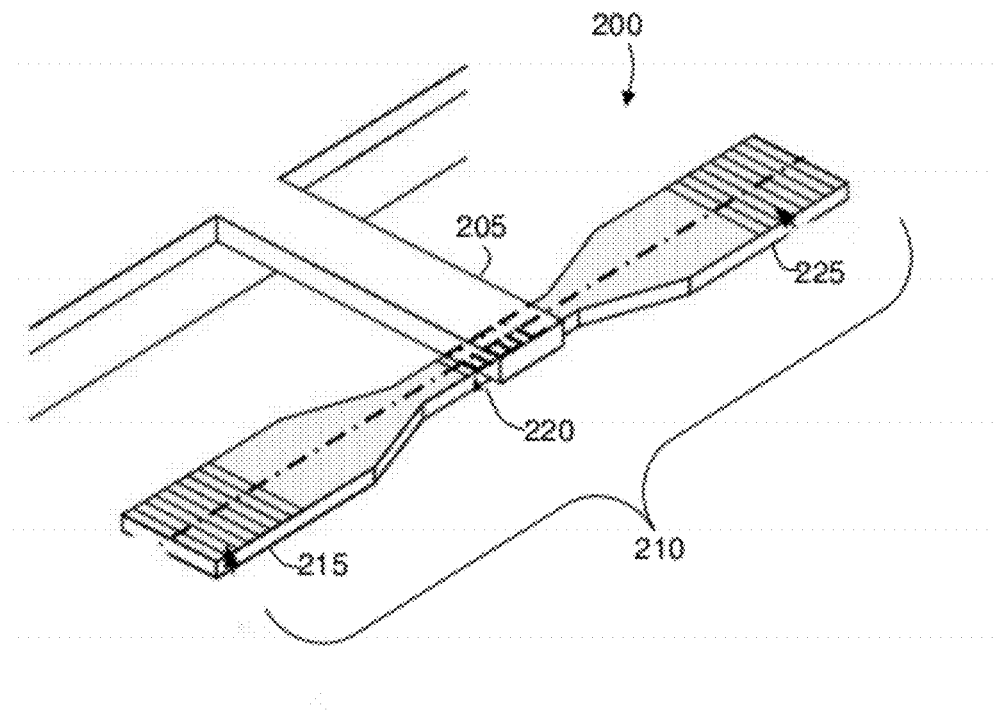
FIG. 2 shows a top perspective view of an optical microcantilever sensor according to an embodiment of the invention.
Figure 3:
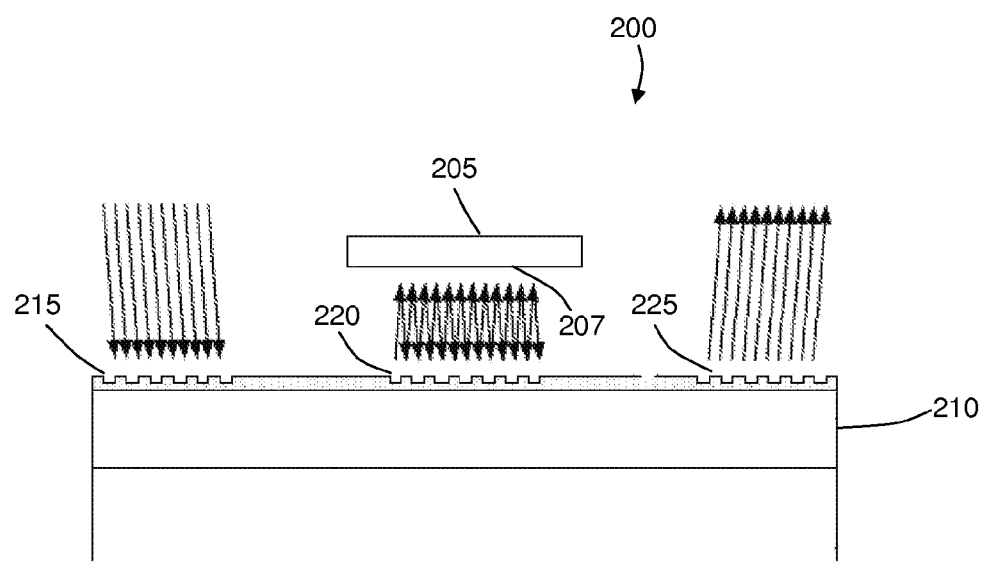
FIG. 3 shows a front sectional view of the optical microcantilever sensor according to an embodiment of the invention.

FIG. 2 shows a top perspective view and FIG. 3 shows a front sectional view of an optical microcantilever sensor 200 according to an embodiment of the invention. As shown in FIG. 2 and FIG. 3, the optical microcantilever sensor 200 comprises a cantilever 205 and a grating coupled resonating structure 210. The grating coupled resonating structure 210 comprises an input grating coupler 215, an interrogating grating coupler 220 and an output grating coupler 225. The interrogating grating coupler 220 is placed directly under and adjacent to the cantilever 205. The cantilever 205 comprises an analyte selective coating and a reflective surface 207, where the reflective surface 207 is opposite the interrogating grating coupler 220.

The input grating coupler 215 is optically connected to the interrogating grating coupler 220 and the interrogating grating coupler 220 is optically connected to the output grating coupler 225. The output grating coupler 225 is optically connected to a signal analyser, for example through an optical fibre.

Referring to FIG. 3, arrows illustrate the light path of the light through the optical microcantilever sensor 200.

Light is coupled to the input grating coupler 215 from a light source, via an optical waveguide or an optical fibre, for example. The light propagates along the grating coupled resonating structure 210 to the interrogating grating coupler 220 and out of the interrogating grating coupler 220 in a near perpendicular direction towards the cantilever 205. The light then propagates along the grating coupled resonating structure 210 to the output grating coupler 225.

The cantilever 205 and interrogating grating coupler 220 form a resonant cavity such that the amount and/or frequency of light coupled to the output grating coupler 225 is a function of the separation of the interrogating grating coupler 220 and the cantilever 205.

The light is output from the grating coupled resonating structure 210 via the output grating coupler 225 so that it may be analysed in real time or stored for analysis at a later time.

When a sample is applied to the cantilever 205, adsorbtion of an analyte may occur depending on the analyte selective coating and a composition of the sample.

A pattern or shape of the interrogating grating coupler 220, for example dimensions of grooves of the interrogating grating coupler 220, determines a modulation of light resonating between the interrogating grating coupler 220 and the cantilever 205. Additionally, a change in distance between the cantilever 205 and the interrogating grating coupler 220 causes a change in the modulation of the light output from the output grating coupler 225.

A change in mass of the cantilever 205 occurs upon adsorbtion of the analyte. In a dynamic mode of operation, the change in mass results in a change in resonance frequency of the cantilever 205 which may be compared to when the analyte is not present. The resonance frequency of the cantilever can be determined at the output grating coupler 225 through resonant excitation of the cantilever 205.

Alternatively, in a static mode of operation, the presence of an analyte causes a change in shape of the cantilever 205. The change in shape of the cantilever 205 causes a change in the distance between the cantilever 205 and the interrogating grating coupler 220a and hence change in the light at the output grating coupler 225.

The signal analyser, which indicates the presence and concentration of the analyte in the sample, uses analysis of the light to estimate the resonance frequency of the cantilever 205, or in the case of a static cantilever the shape of the cantilever 205.

The resonance frequency of the cantilever 205 in dynamic mode operation, or the shape of the cantilever 205 in static mode, may be compared to known characteristics of the cantilever 205 to determine whether an analyte is present or not. Known characteristics of the cantilever 205 include resonance frequency without the presence of an analyte, resonance frequencies with the presence of a particular amount of analyte or concentration, shape without the presence of an analyte, shapes with the presence of a particular amount of analyte or concentration.

In an embodiment of the invention, the resonance frequency, height or position need not be calculated or estimated explicitly for each cantilever and measurement. Predefined signals of the cantilever at, for example, different resonance frequencies, heights or positions may be compared directly to the signal in the analysis step.

Figure 4:
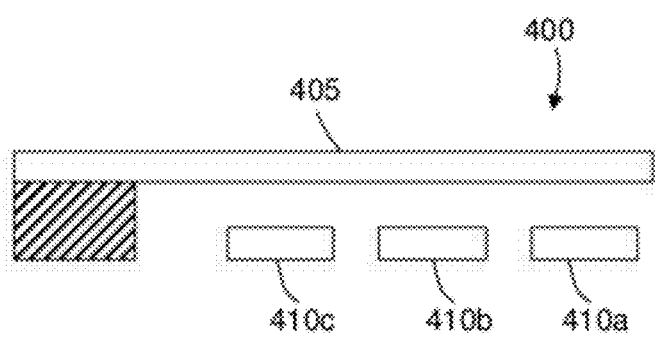
FIG. 4 shows a side sectional view of an optical microcantilever sensor according to a second embodiment of the invention.

FIG. 4 shows a side sectional view of an optical microcantilever sensor 400 according to a second embodiment of the invention. The optical microcantilever sensor 400 comprises a cantilever 405 and a first, second and third grating coupled resonating structure 410a, 410b and 410c, respectively, which are each specific examples of the grating coupled resonating structure 210 of FIG. 2. Similarly, the cantilever 405 is a specific example of the cantilever 205 of FIG. 2.

The first grating coupled resonating structure 410a, placed under a distal end of the cantilever 405, can be used to measure fine changes in shape or fine movements in the cantilever 405.

The second grating coupled resonating structure 410b is positioned adjacent to the first grating coupled resonating structure 410a on an axis substantially parallel to the cantilever 405. The second grating coupled resonating structure 410b, placed under a central part of the cantilever 405, can be used when larger change in shape or larger movements are to be measured, possibly in combination with the first grating coupled resonating structure 410a. In this case the second grating coupled resonating structure 410b provides a refinement of an initial measurement of the first grating coupled resonating structure 410a.

The third grating coupled resonating structure 410c is positioned adjacent to the second grating coupled resonating structure 410b on an axis substantially parallel to the cantilever 405. The third grating coupled resonating structure 410c is placed under a proximal end of the cantilever 405 and can be used when larger change in shape or larger movements are to be measured, possibly in combination with the first and second grating coupled resonating structures 410a and 410b. In this case the second grating coupled resonating structure 410b provides a refinement of the initial measurement of the first grating coupled resonating structure 410a and the refinement provided by the second grating coupled resonating structure 410b.

As would be readily understood by those skilled in the art, any number of grating coupled resonating structures 410 may be placed under a single cantilever, and at any position, without deviating from the present invention.

The exemplary embodiments illustrated in FIG. 2, FIG. 3 and FIG. 4 are applicable to both static and dynamic cantilevers 205, 405, and in both gaseous and aqueous environments. Furthermore, the grating coupled resonating structure 210, 410a, 410b, 410c can be oriented arbitrarily with respect to the cantilever 205, 405, and the design of the cantilever 205, 405 can be decoupled from the design of the grating coupled resonating structure 210, 410a, 410b, 410c. A further valuable capability of this approach is that the multiple grating coupled resonating structures 210, 410a, 410b, 410c under the single cantilever 205, 405, as described in FIG. 4, allows for the shape of the cantilever 205, 405 to be measured with greater precision.

Since an analyte can initially be adsorbed anywhere along the analyte selective coating of the cantilever 205, 405, a change in shape of the cantilever 205, 405 can be used as an early indication of the presence of the analyte. Further, as is discussed further in FIG. 5, it may be advantageous to have multiple grating coupled resonating structures to enhance a dynamic range of the optical microcantilever sensor 200, 300, 400.

Figure 5:
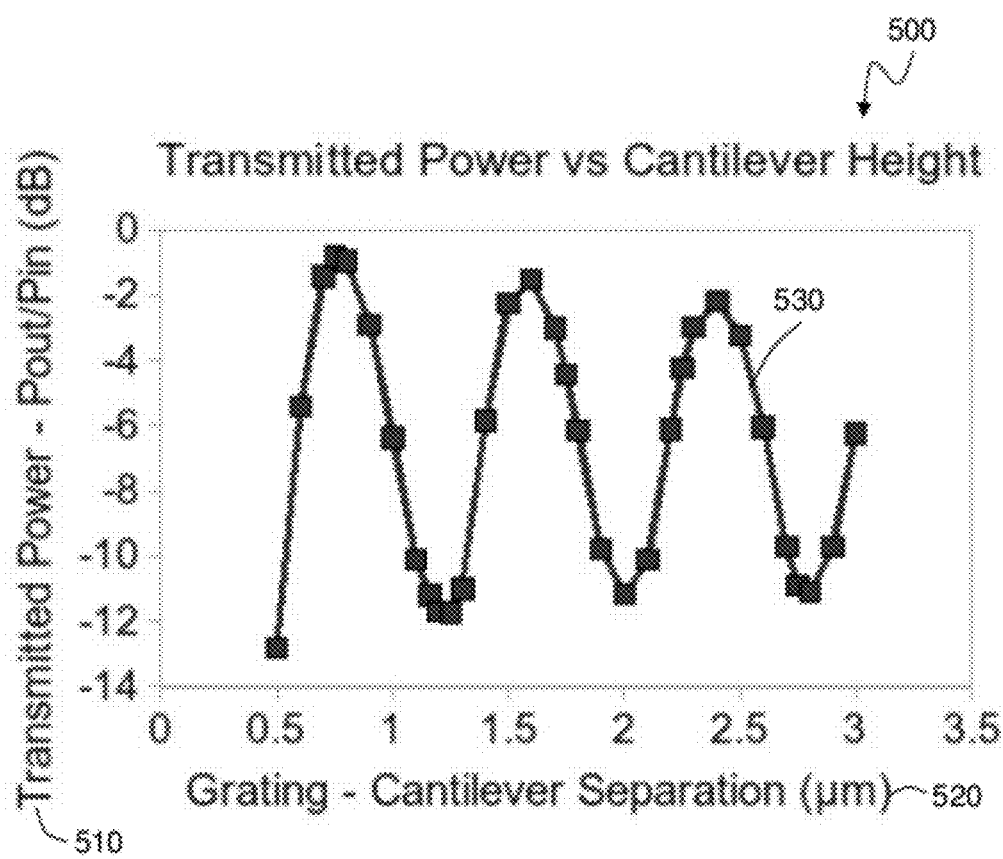
FIG. 5 is a graph showing the periodic nature of a signal of a transmission power according to an embodiment of the invention.

FIG. 5 is a graph 500 showing the periodic nature of a signal 530 of a transmission power 510 according to an embodiment of the invention, with respect to a separation 520 between the cantilever 205, 405 and the grating coupled resonating structure 210, 410a, 410b, 410c. As can be seen in the figure, separations 0.5, 1.25, 2 and 2.75 micrometers, for example, have similar transmission powers 510. This ambiguity can however be removed, while still maintaining high sensitivity, by measuring the displacement of the cantilever 205, 405 at multiple positions. FIG. 4 illustrates an example where multiple grating coupled resonating structures 210, 410a, 410b, 410c are placed under a single cantilever. Such configurations allow for Vernier-like calculations to be made.

Figure 6:
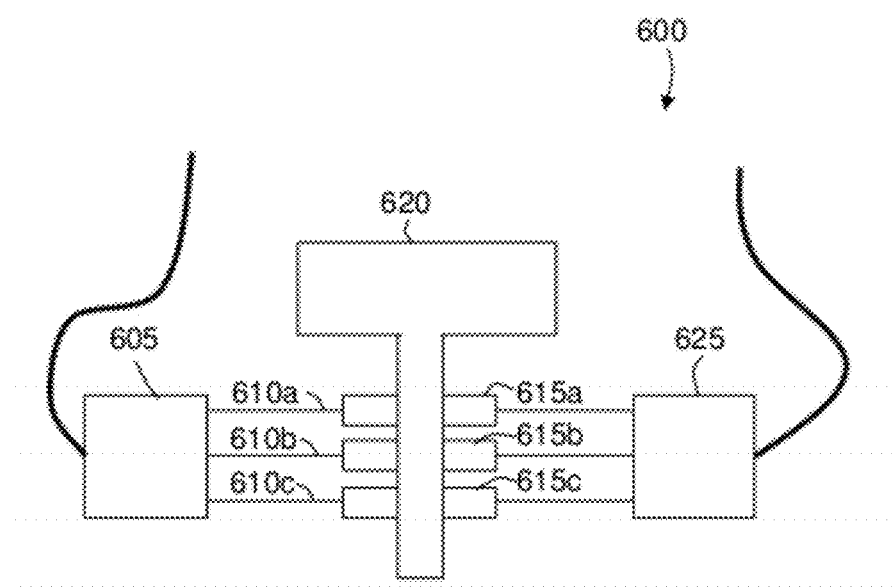
FIG. 6 shows a schematic diagram of an optical microcantilever sensor according to a third embodiment of the invention.

FIG. 6 shows a schematic diagram of an optical microcantilever sensor 600 according to a third embodiment of the invention. The optical microcantilever sensor 600 comprises a wavelength division de-multiplexer 605, the wavelength division de-multiplexer 605 comprising three optical outputs 610a, 610b, 610c, three grating coupled resonating structures 615a, 615b, 615c, a cantilever 620 and a wavelength division multiplexer 625.

An optical input is optically coupled to the wavelength division de-multiplexer 605. The wavelength division de-multiplexer 605 processes light from the optical input and splits the light into a plurality of subsignals, each subsignal having a particular wavelength or plurality of wavelengths. In this example, the wavelength division de-multiplexer 605 has the three optical outputs 610a, 610b, 610c, each carrying light corresponding to a different wavelength or wavelength band.

The optical outputs 610a, 610b, 610c are optically coupled to the grating coupled resonating structures 615a, 615b, 615c. The grating coupled resonating structures 615a, 615b, 615c are similar to the grating coupled resonating structures 210, 410a, 410b, 410c. Each grating coupled resonating structure 615a, 615b, 615c is connected in parallel and forms an optical resonance cavity with the cantilever 620. The wavelength division multiplexer 625 additively combines the light output from grating coupled resonating structures 615a, 615b, 615c such that an output signal of the wavelength division multiplexer 625 comprises a single light signal comprising multiple wavelengths.

Analysis of an individual grating coupled resonating structure 615a, 615b, 615c, may be performed by using pre-known characteristics of the grating coupled resonating structure 615a, 615b, 615c. These characteristics include, for example, a wavelength throughput of the grating coupled resonating structure 615a, 615b, 615c.

Figure 7:
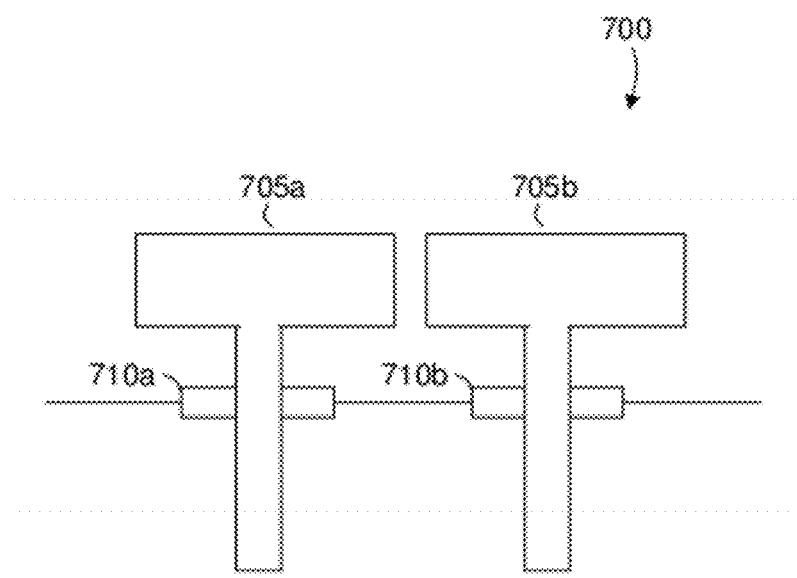
FIG. 7 shows a schematic diagram of an optical microcantilever sensor according to a fourth embodiment of the invention.

FIG. 7 shows a schematic diagram of an optical microcantilever sensor 700 according to a fourth embodiment of the invention. The optical microcantilever sensor 700 comprises two cantilevers 705a, 705b and two grating coupled resonating structures 710a, 710b.

The grating coupled resonating structures 710a, 710b form resonant cavities with the cantilevers 705a, 705b. The grating coupled resonating structure 710a is optically coupled to the grating coupled resonating structure 710b in series, i.e. an output of the first grating coupled resonating structures 710a is connected in an input of the second grating coupled resonating structures 710b.

Cantilever and grating coupled resonating structure pairs, for example 705a and 710a, or 705b and 710b, may be analysed individually. This is advantageous as each pair may be sensitive to a different analyte. The analysis may be performed by using pre-known characteristics of the grating coupled resonating structure 710a, 710b or the cantilever 705a, 705b. These characteristics include, for example, a resonance frequency of the cantilever 705a, 705b and a wavelength throughput of the grating coupled resonating structure 710a, 710b given a separation to the cantilever 705a, 705b.

Figure 8:
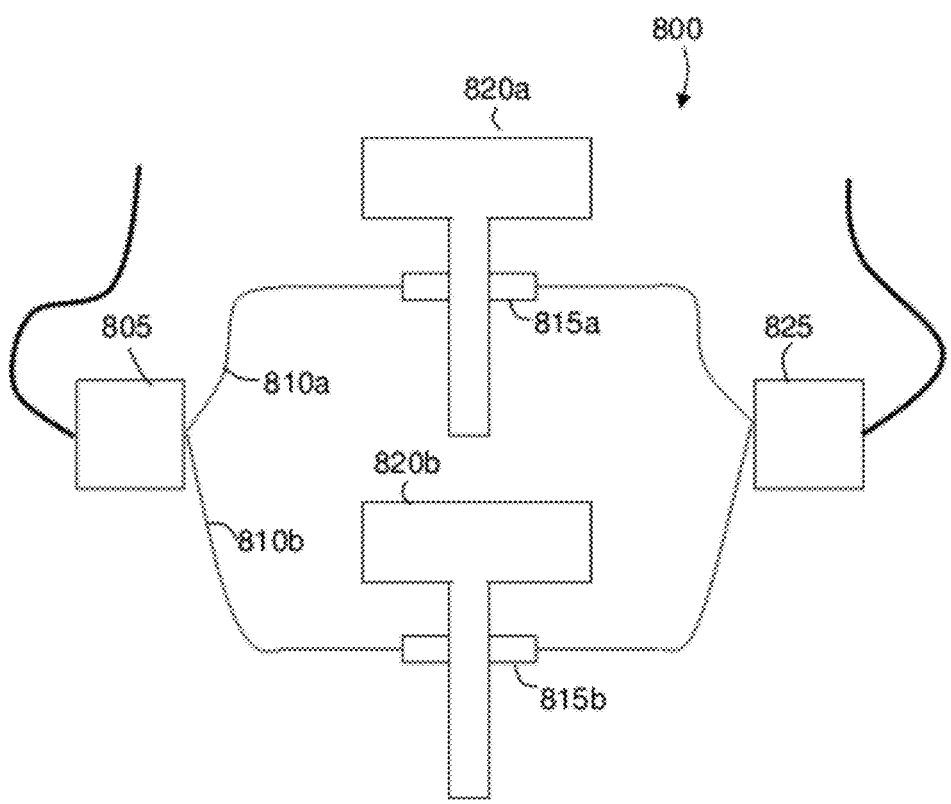
FIG. 8 shows a schematic diagram of an optical microcantilever sensor according to a fifth embodiment of the invention.

FIG. 8 shows a schematic diagram of an optical microcantilever sensor 800 according to a fifth embodiment of the invention.

The optical microcantilever sensor 800 comprises a wavelength division de-multiplexer 805, the wavelength division de-multiplexer 805 comprising two optical outputs 810a, 810b, two grating coupled resonating structures 815a, 815b, two cantilevers 820a, 820b and a wavelength division multiplexer 825.

An optical input is optically coupled to the wavelength division de-multiplexer 805. The wavelength division de-multiplexer 805 processes light from the optical input and splits the light into a plurality of subsignals, each subsignal having a particular wavelength or plurality of wavelengths. In this example, the wavelength division de-multiplexer 805 has the two optical outputs 810a, 810b, each carrying light corresponding to a different wavelength or wavelength band.

The optical outputs 810a, 810b are optically coupled to the grating coupled resonating structures 815a, 815b respectively. The grating coupled resonating structures 815a, 815b are similar to the grating coupled resonating structures 210, 410a, 410b, 410c, 615a, 615b. Each grating coupled resonating structure 815a, 815b forms an optical resonance cavity with the cantilevers 820a, 820b, respectively. The wavelength division multiplexer 825 additively combines the light output from grating coupled resonating structures 815a, 815b such that an output signal of the wavelength division multiplexer 825 comprises a single light signal comprising multiple wavelengths.

Analysis of an individual cantilever grating coupled resonating structure combination, for example 815a/820a or 815b/820b, which are connected in parallel, may be performed by using pre-known characteristics of the grating coupled resonating structure 815a, 815b or the cantilever 820a, 820b. These characteristics include, for example, a resonance frequency of the cantilever 820a, 820b and a wavelength throughput of the grating coupled resonating structure 815a, 815b.

Figure 9:
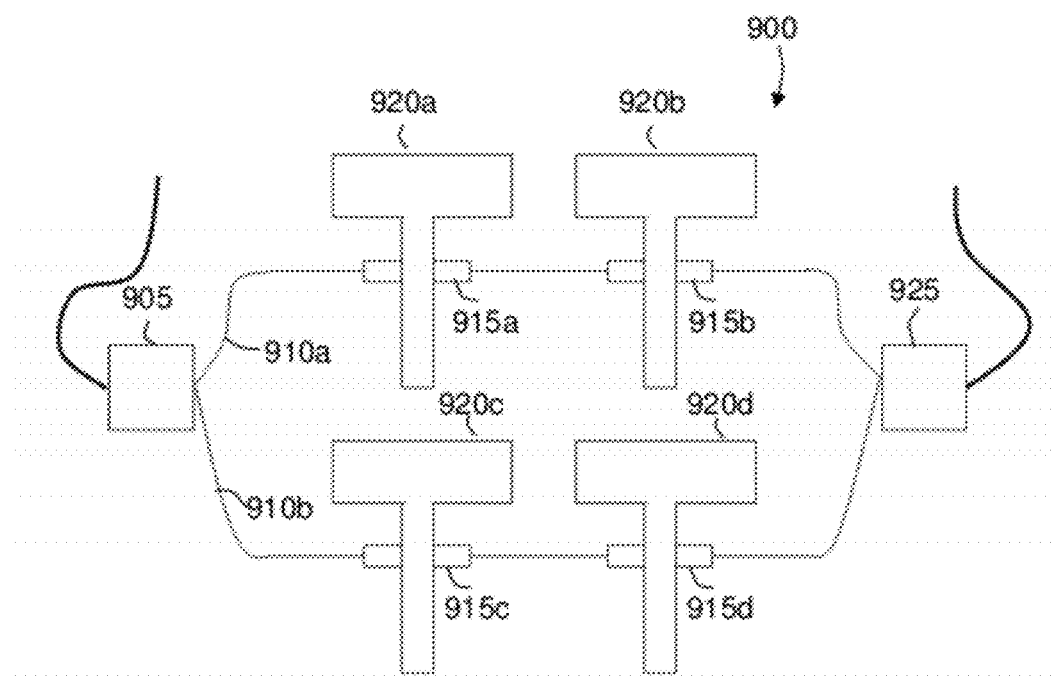
FIG. 9 shows a schematic diagram of an optical microcantilever sensor 900 according to a sixth embodiment of the invention.

FIG. 9 shows a schematic diagram of an optical microcantilever sensor 900 according to a sixth embodiment of the invention.

The optical microcantilever sensor 900 comprises a wavelength division de-multiplexer 905, the wavelength division de-multiplexer 905 comprising two optical outputs 910a, 910b, four grating coupled resonating structures 915a, 915b, 915c, 915d, four cantilevers 920a, 920b, 920c, 920d and a wavelength division multiplexer 925. The optical microcantilever sensor 900 is similar to the embodiments described in FIG. 7 and FIG. 8, except for that the cantilevers 920a, 920b, 920c, 920d and grating coupled resonating structures 915a, 915b, 915c, 915d are coupled in a series and parallel configuration.

The terms 'series' and 'parallel' are used in this specification. Series refers to the case where an output of a first grating coupled resonating structure is optically connected to an input of a second grating coupled resonating structure. Parallel refers to the case where an input is shared between a first and second grating coupled resonating structure. Parallel connections include the case where the first grating coupled resonating structure uses or modifies a first part of the input, and the second grating coupled resonating structure uses or modifies a second part of the input, even where a series physical connection exists.

Additionally, as is understood by a person skilled in the art, any number of parallel and series connections may exist on a single sensor.

As will be understood by those having ordinary skill in the art, in light of the present description, advantages of the present invention include the ability to economically have a very large amount of sensors on a small surface, enabling efficient detection on multiple analytes. Furthermore, the detection of analytes with high precision and fidelity is possible. These efficient sensors may be used for the efficient and economical detection of pesticides or other chemicals in food, for efficient detection of explosives, narcotics or other elicit substances just to name a few examples.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

Limitations in the patent claims should be interpreted broadly based on the language used in the claims, and such limitations should not be limited to specific examples described herein. In this specification, the terminology "present invention" is used as a reference to one or more aspects within the present disclosure. The terminology "present invention" should not be improperly interpreted as an identification of critical elements, should not be improperly interpreted as applying to all aspects and embodiments, and should not be improperly interpreted as limiting the scope of any patent claims.

What is claimed is:

1. An apparatus for detecting a presence of one or more analytes in a sample, said apparatus comprising:
   a first cantilever comprising an analyte selective coating that is selective to said one or more analytes; and
   a first grating coupled resonating structure positioned adjacent to said cantilever, comprising a first interrogating grating coupler, said first interrogating grating coupler configured to direct light towards the first cantilever;
   wherein said first interrogating grating coupler and said cantilever form an optical resonant cavity therebetween.

2. The apparatus of claim 1 wherein said first cantilever is dynamic.

3. The apparatus of claim 1 where said first cantilever is static.

4. The apparatus of claim 1, further comprising:
   a second grating coupled resonating structure comprising a second interrogating grating coupler;
   wherein said second interrogating grating coupler and said first cantilever form an optical resonant cavity.

5. The apparatus of claim 4 wherein said second grating coupled resonating structure is positioned adjacent to said first grating coupled resonating structure on an axis substantially parallel to said first cantilever.

6. The apparatus of claim 1 further comprising a signal analyser optically coupled to said first grating coupled resonating structure for detection of said presence of one or more analytes in said sample.

7. The apparatus of claim 6, wherein said signal analyser compares light modulated by said first grating coupled resonating structure and said first cantilever with a plurality of predefined signals.

8. The apparatus of claim 4 wherein said first grating coupled resonating structure provides an initial measurement, and said second grating coupled resonating structure provides a refinement of said initial measurement.

9. The apparatus of claim 4 wherein said first grating coupled resonating structure and said second grating coupled resonating structure are used to determine a shape of said first cantilever.

10. The apparatus of claim 1, further comprising:
    a second cantilever;
    a second grating coupled resonating structure comprising a second interrogating grating coupler;
    wherein said second interrogating grating coupler and said second cantilever form an optical resonant cavity.

11. The apparatus of claim 10, wherein said first grating coupled resonating structure and said second grating coupled resonating structure are optically coupled in series.

12. The apparatus of claim 10, wherein said first grating coupled resonating structure and said second grating coupled resonating structure are optically coupled in parallel.

13. The apparatus of claim 1, wherein said first cantilever comprises a reflective surface that forms part of the optical resonant cavity.

14. A method of detecting the presence of one or more analytes in a sample, said method comprising the steps of:
- applying said sample to a cantilever, wherein said cantilever comprises an analyte selective coating selective to said one or more analytes;
- passing an optical signal through a grating coupled resonating structure, said grating coupled resonating structure positioned adjacent to said cantilever and including an interrogating grating coupler, said interrogating grating coupler configured to direct light towards the first cantilever, wherein said interrogating grating coupler and said cantilever form an optical resonant cavity therebetween; and
- analysing said optical signal output from the grating coupled resonating structure.

15. The method of claim 14 wherein said cantilever is static, and the analysis step comprises determining a deflection of said cantilever.

16. The method of claim 14 wherein said cantilever is dynamic, and said step of analysing said optical signal comprises determining the resonance frequency of the cantilever and comparing the resonance frequency to known resonant characteristics of the cantilever.

17. The method of claim 14 wherein said step of analysing said optical signal comprises comparing said optical signal to a plurality of predefined signals.

18. The method of claim 14, further comprising the step of passing a second optical signal through a second grating coupled resonating structure, wherein said second grating coupled resonating structure is arranged to form a resonant cavity with said cantilever, and analysing said second optical signal.

19. The method of claim 18 wherein said step of analysing said optical signal comprises estimating an initial cantilever deflection measurement, and said step of analysing said second optical signal comprises refining said initial cantilever deflection measurement.

20. The method of claim 18, further comprising the step of estimating a shape of said cantilever, wherein said step of analysing said optical signal comprises estimating a cantilever deflection measurement at a first position, and said step of analysing said second optical signal comprises estimating a cantilever deflection measurement at a second position.

* * * * *